United States Patent [19]

Ellendt et al.

[11] 4,414,074
[45] Nov. 8, 1983

[54] PROCESS FOR THE PURIFICATION OF 4,4'-DIISOCYANATODIPHENYLMETHANE BY PLURAL DISTILLATIONS

[75] Inventors: Günther Ellendt; Günter Gleitsmann, both of Krefeld; Max Scheidel, Willich, all of Fed. Rep. of Germany

[73] Assignee: Bayer Aktiengesellschaft, Leverkusen, Fed. Rep. of Germany

[21] Appl. No.: 436,489

[22] Filed: Oct. 25, 1982

[30] Foreign Application Priority Data

Nov. 12, 1981 [DE] Fed. Rep. of Germany ....... 3145010

[51] Int. Cl.³ ...................... B01D 3/10; C07C 119/00
[52] U.S. Cl. ...................................... 203/21; 203/74; 203/77; 260/453 SP
[58] Field of Search .............. 203/74, 77, 75, 20, 203/71, 81, 21, 27, 91; 260/453 SP, 453 AR

[56] References Cited

U.S. PATENT DOCUMENTS

| | | | |
|---|---|---|---|
| 3,155,699 | 11/1964 | Powers | 260/453 |
| 3,471,543 | 10/1969 | Sayigh | 260/453 |
| 3,658,656 | 4/1972 | Adica et al. | 260/453 SP |
| 3,816,496 | 6/1974 | Schnabel | 260/453 SP |
| 3,892,634 | 7/1975 | Hajek et al. | 203/72 |
| 3,912,600 | 10/1975 | Hatfield et al. | 260/453 SP |
| 4,118,286 | 10/1978 | Burns et al. | 260/453 SP |
| 4,189,354 | 2/1980 | Ellendt et al. | 203/81 |
| 4,264,723 | 4/1981 | Ichijima et al. | 430/555 |

FOREIGN PATENT DOCUMENTS 1229181 4/1971 United Kingdom .
1263439 2/1972 United Kingdom .

Primary Examiner—Wilbur L. Bascomb, Jr.
Attorney, Agent, or Firm—Gene Harsh; Joseph C. Gil; Richard A. Elder

[57] ABSTRACT

A new process for the production of very pure 4,4'-diisocyanatodiphenylmethane is disclosed, in which diisocyanatodiphenylmethane isomers which are obtained by distillation from the phosgenation products of aniline/formaldehyde condensates are initially freed from 2,2'- and 2,4'-isomers under certain distillation conditions and are then further worked-up by distillation, in that in a first final stage, from 50 to 90%, by weight of the diisocyanate freed from 2,2'- and 2,4'-isomers is isolated as the head product in the form of pure 4,4'-diisocyanatodiphenylmethane and in a second final stage, another quantity of pure 4,4'-diisocyanatodiphenylmethane is separated as the head product from the distillation of the sump of the first final stage.

5 Claims, 3 Drawing Figures

PROCESS FOR THE PURIFICATION OF 4,4'-DIISOCYANATODIPHENYLMETHANE BY PLURAL DISTILLATIONS

This invention relates to a new distillation process for working-up polyisocyanate mixtures of the diphenylmethane series, which have been obtained by phosgenating aniline/formaldehyde condensates, in order to produce very pure 4,4'-diisocyanatodiphenylmethane.

BACKGROUND OF THE INVENTION

The polyisocyanate mixtures of the diphenylmethane series resulting from the condensation of aniline and formaldehyde in the presence of acid catalysts followed by phosgenation of the resulting polyamine mixtures, contain, in addition to the isomers and higher homologues of diisocyanatodiphenylmethane, varying quantities of impurities, for example, of monoisocyanates, colored impurities and compounds having organically-bound chlorine. Some of these latter compounds contain the chlorine in a more-or-less readily-separable form, called hydrolyzable chlorine, although these compounds are present with compounds having less readily-separable chlorine, also. It is known that these different chlorine compounds influence the reaction of isocyanates with polyols to produce polyurethanes, and that they act in particular, on the rate of the reaction between the isocyanates and polyols. It is particularly desirable in the case of 4,4'-diisocyanatodiphenylmethane, which is used in large quantities for the production of elastic polyurethanes, to limit the effect of the organic chlorine compounds influencing the polyurethane reaction, or, at least, to standardize the effect by controlling the chlorine content of these products. Thus, the content of chlorine in these compounds is an important parameter for the purity of 4,4'-diisocyanatodiphenylmethane.

It is also desirable and necessary to reduce the amount of monoisocyanates, such as phenyl-isocyanate which originates from the residual contents of aniline in the polyamine mixtures used in the phosgenation process to as low a level as possible. This is because phenylisocyanate raises problems of working hygiene during the processing and handling of the isocyanates of the diphenylmethane series, due to its low vapor pressure and high toxicity.

A number of processes are known for removing these impurities in order to attain the required degree of purity of the diisocyanatodiphenylmethanes. It has been proposed, for example, to convert the compounds containing chlorine into almost nonvolatile forms by adding certain substances (for example, see German Pat. No. 1,138,040), then to remove the impurities. Another proposal (German Offenlegungsschrift No. 1,938,384) is based on the use of a complex commercial crystallization process. Also, processes for the distillative purification of diisocyanatodiphenylmethanes have been widely used on a commercial scale.

In the known distillation processes (see, for example, German Auslegeschriften Nos. 2,631,168 and 1,923,214 and U.S. Pat. Nos. 3,892,634 and 3,471,543), the diisocyanatodiphenylmethane isomers are usually separated from their higher homologues in a first distillation step. In a second step, the isomeric diisocyanatodiphenylmethanes are separated, with the more readily-volatile 2,2'- or 2,4'-isomers accumulating as head products and the 4,4'-isomer remaining as the sump product.

The 4,4'-diisocyanatodiphenylmethane, which is substantially freed of isomers, is then distilled off again in a final distillation to remove polymerization products which have formed due to the thermal effects of the distillation process.

Another separating step may be added in each case for separating readily- and much less volatile impurities, according to German Auslegeschrift No. 2,631,168. This process allows low chlorine contents to be obtained in the end product when there is a low content of chlorine compounds in the isocyanate mixture which is fed into the distillation. The process is not reliable enough, however, to result in the low chlorine contents required in the end product when there are higher chlorine contents in the original isocyanate mixture.

In order to economize on the number of distillation columns, it has also been proposed (German Offenlegungsschrift No. 2,944,601) to carry out, in the same column, the isomer separation step and the final distillation by side flow removal, with the content of chlorine compounds being reduced by introducing inert gas as an entrainer. This process does not provide a solution to the problem, however, as distillates are obtained which have dimer contents in the vicinity of their saturation limits in diisocyanatodiphenylmethane, i.e., products are produced which are either already cloudy during distillation or which become cloudy shortly thereafter,- due to the precipitation of dimers.

A new method for obtaining particularly pure 4,4'-diisocyanatodiphenylmethane is now indicated by the process according to the present invention.

DESCRIPTION OF THE INVENTION

Figure 1:
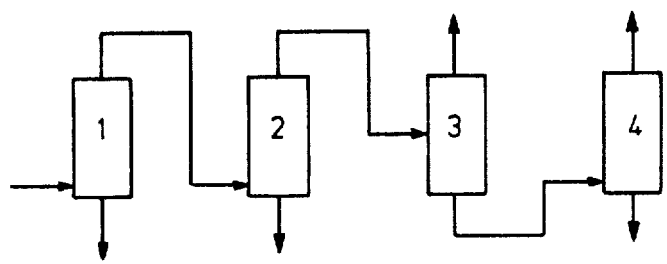
FIG. 1 Schematic of the stages of distillation purification according to known processes.

The present invention is directed to a process for the production of very pure 4,4'-diisocyanatodiphenylmethane by the distillative separation of diisocyanatodiphenylmethane isomers from a polyisocyanate mixture of the diphenylmethane series which has been obtained by phosgenating aniline/formaldehyde condensates. In this process, the head product of a first distillation step is further distilled in a second distillation stage, with from 0.5 to 20%, by weight, of the quantity of product introduced into this second stage being drawn off as the sump of the second stage. The 2,2'- and 2,4'-diisocyanatodiphenylmethane from the head product of the second stage is separated from the remaining product in a subsequent third distillation stage and the sump product of this third stage is worked up by further distillation to obtain very pure 4,4'-diisocyanatodiphenylmethane. This process is particularly characterized in that:

(a) the temperatures of the condenser outlets of the first three distillation stages are adjusted to from 130° to 230° C., such that the temperatures are from 10° to 50° C. below the incoming vapor temperature of the feed product, which is predetermined by the vacuum in the distillation column, and (b) the sump remaining in the third stage is worked up in two final stages, such that in a first final stage, from 50 to 90%, by weight, of the sump of the third stage is isolated as the head product in the form of pure 4,4'-diisocyanatodiphenylmethane, and in a second final stage, the sump of the first final stage is split, by distillation, into additional pure 4,4'-diisocyanatodiphenylmethane as the head product and a distillation residue as the sump.

The process according to the present invention will first be explained in more detail with reference to the drawings. In the drawings, FIGS. 1 and 2 correspond to the previously known processes according to German Auslegeschrift No. 2,631,168.

FIG. 1 illustrates an embodiment for the distillative working-up operation of polyisocyanate mixtures of the diphenylmethane series. In a column (1), a distillate containing the main 4,4'-diisocyanatodiphenylmethane product, in addition to the 2,2'- and 2,4'-isomers is obtained from a polyisocyanate mixture of the diphenylmethane series with higher homologues of the series remaining as the sump. The head product still contains impurities, the boiling point of this head product being closely above or below that of the diisocyanatodiphenyldimethane isomers. The distillate is then re-distilled in column (2), a small quantity of the sump which contains quantities of impurities which have a higher boiling point than diisocyanatodiphenylmethane and which have been entrained during the first distillation step being removed.

The distillate from column (2), is introduced into column (3) where an isomer mixture mainly containing 2,4'-diisocyanatodiphenylmethane is obtained as the head product. The previously purified 4,4'-diisocyanatodiphenylmethane discharged from the sump of column (3) is then freed, by distillation in column (4), from the impurities resulting from the earlier distillation thermal treatments. The distillate of column (4) is a 4,4'-diisocyanatodiphenylmethane having some content of chlorine compounds.

In this process, the content of low-boiling compounds which particularly contain chlorine is still high in the distillate of column (3) (not surprisingly, since German Auslegeschrift No. 2,631,168 is a process for adjusting organic chlorine contents). Due to the degree of purity of the distillate from column (3) which is achieved in this case, it must be assumed that the condenser discharge temperatures of columns (1) to (3) are <120° C.

Figure 2:
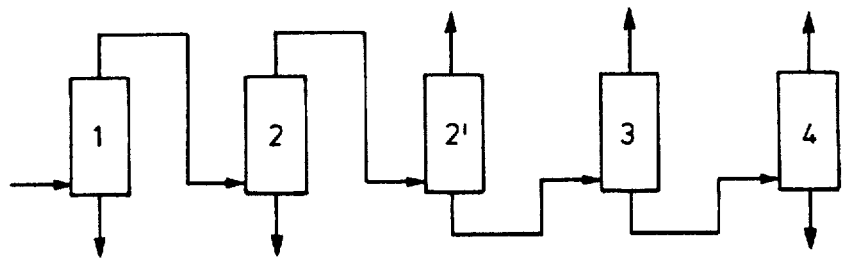
FIG. 2 Schematic of the stage of distillation purification of an improvement over FIG. 1 process.

FIG. 2 illustrates an improved embodiment of the prior art process. In this case, by connecting column (2') between columns (2) and (3), a head product is removed at column (2'), which product mainly contains, in addition to 2,2'- and 2,4'-diisocyanatodiphenylmethane, compounds having boiling points which are lower than the diisocyanatodiphenylmethane isomers, so that low chlorine contents may be established in the distillate of column (3). Nevertheless, this variation of the prior art process still produces more or less high chlorine contents in the distillate of column (4).

Figure 3:
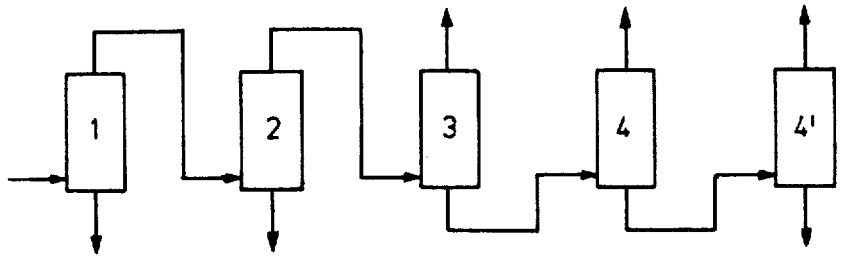
FIG. 3 Schematic of the stages of the process according to the invention.

FIG. 3 provides an illustration of the novel process according to the present invention.

A polyisocyanate mixture of the diphenylmethane series is fed into distillation stage (1) and is separated into a sump product containing higher homologues and a crude diisocyanatodiphenylmethane isomer mixture. The distillation operation in stage (1) is generally a single distillation without reflux. Of course, the distillation in stage (1) could also be carried out using a distillation column with reflux, although this, as mentioned, is unnecessary. The distillate is condensed such that the temperature of the condenser outlet is from 130° to 230° C., preferably from 130° to 200° C., and, in particular, from 140° to 160° C.

The amount of distillate which is distilled off in stage (1) depends on the nature of the feed and on the viscosity which the sump product shall have. It may vary within very wide limits and is not at all essential.

Impurities of the distillate of stage (1) which have a higher boiling point than the diisocyanatodiphenylmethane isomers are separated by distillation in stage (2) which comprises one or more distillation columns and is connected downstream of distillation stage (1). The distillation in stage (2) is carried out in a reflux ratio (reflux ratio=weight ratio of reflux to weight of distillate removed) of from 0.1:1 to 10:1, preferably from 0.3:1 to 3:1. From 0.5 to 20, preferably from 1 to 10%, by weight, of the mixture introduced into stage (2) is continuously removed by sluicing from the sump of stage (2). The main quantity of product is distilled over the head of stage (2), the condensation temperature corresponding to the temperatures stated above.

The 2,2'- and 2,4'-isomers contained in the distillate of stage (2) are separated by distillation in stage (3), which also comprises one or more distillation columns and is connected downstream of stage (2). Distillation stage (3) is operated in a reflux ratio of from 2:1 to 45:1, preferably from 15:1 to 30:1. The condensation temperature is adjusted in this case within the ranges described above.

The previously-purified 4,4'-diisocyanatodiphenylmethane remaining as the sump of distillation stage (3) is finally purified by distillation in final stages (4) and (4'). The distillation in stage (3) is carried out so that the sump product of stage (3) has a maximum content of 2,4'-diisocyanatodiphenylmethane of 3% by weight.

For the purpose of further purification of the sump of stage (3), from 50 to 90%, by weight, of the sump remaining from stage (3) is distilled over head in the form of pure 4,4'-diisocyanatodiphenylmethane in the first final stage (4), which is preferably operated in a reflux of from 0.2:1 to 2:1. The distillate containing less than 5 ppm of phenylisocyanate and less than 5 ppm of hydrolyzable chlorine is preferably cooled to below 50° C. immediately after leaving the first final stage (4). Stage (4) may, in principle, also comprise one or more distillation columns connected in series, the sump of the column connected upstream being fed in each case into the column connected downstream. If several columns are used at stage (4), above condition that from 50 to 90% by weight of the sump resulting in stage (3) is distilled off over head in the form of pure 4,4'-diisocyanatodiphenylmethane in the first final stage (4) refers to the sum of all columns of stage (4).

The sump of stage (4), i.e., if a single distillation column is used, the sump of this single column, or if several columns connected in series are used, the sump of the last of these columns, is introduced into the last final stage (4'). There, it is split by distillation into additional pure 4,4'-diisocyanatodiphenylmethane as the head product and into from about 5 to 15%, by weight, of sump product, based on the total quantity of the sump of stage (1). The reflux ratio of stage (4') comprising a single distillation column is from 0.2:1 to 3:1, preferably from 0.2:1 to 1:1. The quality of the 4,4'-diisocyanatodiphenylmethane obtained as the head product corresponds to the quality of the head product of stage (4). In this case as well, the head product is cooled to below 50° C., preferably immediately after leaving the column.

This cooling operation substantially prevents the formation of dimers. The sump remaining from the last final stage (4') contains the impurities which have formed due to the thermal strain, and also contains such impurities containing chlorine which have a higher boiling point than the 4,4'-diisocyanatodiphenylmethane.

According to a particular embodiment of the present process, the condensation heat evolving in the condensers of the distillation stages may be used for recovering vapor in a pressure stage from 2 to 16 bars. For this purpose, the condensers are operated with water under a pressure selected according to the discharge temperature of the condensates.

The distillation stages which are used in the present process may comprise, in each case, one or more distillation units, with the exception of the last final stage (4'), which comprises only one distillation unit, whereby particularly in the case of the distillation stages (2), (3), (4) and (4'), effectively divided distillation columns are used. In the case of distillation stages (1) to (3), the temperature of the condenser outlets must be within the range specified, i.e., from 130° to 230° C., preferably from 130° to 200° C., and, in particular, from 140° to 160° C., and the second condition, i.e., that the temperature of the condenser outlets be from 10 to 50° C., preferably from 20° to 40° C. below the incoming vapor temperature, as predetermined in each case according to the vacuum in the column, must simultaneously always be met. The distillation stages (4) and (4') may also be operated according to these conditions, but the cooling of the distillates to below 50° C. should take place directly at the outlet of the condensers.

The process according to this invention has, in particular, the following advantages over the nearest prior art process according to German Auslegeschrift No. 2,631,168:

(a) By adjusting the product discharge temperatures to values above 130° C., readily-volatile impurities, such as phenylisocyanate or compounds having organically-bound chlorine, may be degassed from the distillates and removed via the vacuum system. This measure enables the production of very pure 4,4'-diisocyanatodiphenylmethane, while not having to use the distillation stage (2') shown in FIG. 2.

(b) Also, as is known, the distillative purification of diisocyanatodiphenylmethane is not a simple distillative purification or separating process of impurities, but instead, is complicated by the thermal strain on the products. This thermal strain causes the isocyanate to decompose, resulting in yield losses, or the splitting of impurities containing organically-bound chlorine which may then recombine into other compounds, to some extent having higher boiling points. These changes create a fluctuating content of hydrolyzable chlorine in the distillate of stage 4 of FIG. 2 according to the prior art processes, when the chlorine level in the inlet of the columns connected upstream increases. By the process according to the present invention, a 4,4'-diisocyanatodiphenyl methane is obtained which has constant, extremely low chlorine contents.

In order to separate chlorine compounds having boiling points closely above that of 4,4'-diisocyanatodiphenylmethane according to the present process, the previously purified 4,4'-diisocyanatodiphenylmethane is distilled in a two-stage distillation. Fifty to 90% of the sump from stage (3) is distilled off in the first final state (4), with a greatly reduced residence time in the sump, and thus with a reduced thermal strain. From 10 to 50% of the sump from stage (3) remains in the sump of stage (4). The large quantity of product from the sump of stage (4) which is removed to stage (4'), together with the reflux ratio of from 0.2:1 causes an excellent separation of the chlorine compounds, while simultaneously avoiding the formation of new impurities. The remaining 4,4'-diisocyanatodiphenylmethane is then distilled off in stage (4') connected downstream, and from 5 to 15% of the product introduced is removed from the sump. In stage (4'), the residence time and thus the thermal strain on the 4,4'-diisocyanatodiphenylmethane are also lower compared to the prior art process, so that in this case, not more than 5 ppm of hydrolyzable chlorine is obtained in the distillate.

The distillates of stages (3), (4) and (4') obtained by the process according to the present invention are of an extreme degree of purity, particularly with respect to the content of phenylisocyanate, to compounds having organically-bound chlorine and to impurites which result in high discoloration under the effect of light and air. A particular advantage of this process is the fact that this degree of purity may even be achieved when there are fluctuating contents of impurities in the isocyanate mixture used as the starting material. Moreover, anti-discoloration stabilizers must only be added infrequently to the resulting products.

The following Examples in which all the percentages are based on weight, are to explain the process according to the present invention in more detail. The following Examples 1 and 2 are comparison examples according to the teaching of German Auslegeschrift No. 2,631,168. In these comparison examples the discharge temperatures in stages (1), (2), (2') and (3) are from about 100° C. to about 110° C. which means that the temperature of the condenser outlets is about 75° C. below the incoming vapor temperatures.

EXAMPLES

EXAMPLE 1 (FIG. 1)

Example 1 represents a known process for the separation of products having boiling points higher than that of diisocyanatodiphenylmethane.

A polyisocyanate mixture of the diphenylmethane series, approximately containing:

5.6% of 2,4'-diisocyanatodiphenylmethane,
80.4% of 4,4'-diisocyanatodiphenylmethane,
12.8% of 3-nuclear compounds, and
1.2% of 4- and higher nuclear compounds, is worked up in a continuously-operating distillation plant which comprises stages (1), (2), (3) and (4) of FIG. 1. These stages are distillation units comprising rotary evaporators with corresponding circulatory pumps, condensers for the distillate and a connection to a suitable vacuum system. A column is connected between the evaporator and condenser at (2), (3) and (4).

The chlorine contents which may be obtained in the distillates with a varying inlet quantity and quality of the product feed into the distillation unit (1) are represented as follows:

TABLE 1

A process for the separation of impurities having a higher boiling point than diisocyanatodiphenylmethane isomers (MDI).

| Distillate of column (FIG. 1) | Product kg/h | Reflux kg/h | Hydrolyzable chlorine ppm | Total chlorine ppm |
|---|---|---|---|---|
| 1 | 1,255 | | 359 | 741 |

TABLE 1-continued

A process for the separation of impurities having a higher boiling point than diisocyanatodiphenylmethane isomers (MDI).

| Distillate of column (FIG. 1) | Product kg/h | Reflux kg/h | Hydrolyzable chlorine ppm | Total chlorine ppm |
|---|---|---|---|---|
|   | 950 | — | 240 | 570 |
| 2 | 1,715 | 800 | 152 | 360 |
|   | 850 | 800 | 160 | 280 |
| 3 | 178 | 2,000 | 214 | 450 |
|   | 75 | 1,200 | 115 | 280 |
| 4 | 1,010 | 800 | 25 | 60 |
|   | 740 | 800 | 4 | 12 |

EXAMPLE 2 (FIG. 2)

As Example 1, but supplemented by a distillation stage (2') for separating readily-volatile impurities.

In order to separate by-products of a boiling point below that of 4,4'-diisocyanatodiphenylmethane, another stage (2') was connected which, like stage (3), comprises an evaporator, a column packing and a condenser.

The data listed in the Table represent the quality of the distillate according to measured chlorine contents.

TABLE 2

| Distillate of column (FIG. 2) | A process for the separation of impurities with higher and lower boiling points than MDI. | | | |
|---|---|---|---|---|
|   | Product kg/h | Reflux kg/h | Hydrolyzable chlorine ppm | Total chlorine ppm |
| 1 | 1,690 | — | 460 | 820 |
|   | 1,200 | — | 280 | 530 |
| 2 | 1,650 | 1,200 | 250 | 410 |
|   | 1,170 | 1,200 | 170 | 320 |
| 2' | 50 | 2,000 | 2,400 | 3,760 |
|   | 45 | 2,000 | 1,640 | 2,985 |
| 3 | 250 | 4,000 | 4 | 20 |
|   | 170 | 4,000 | 10 | 35 |
| 4 | 1,330 | 1,200 | 29 | 55 |
|   | 925 | 1,200 | 5 | 18 |

EXAMPLE 3 (FIG. 3)

Example 3 represents a process according to the present invention in which a polyisocyanate mixture of the composition according to Example 1 is worked up in a continuously-operating distillation plant, comprising stages (1), (2), (3), (4) and (4') (FIG. 3).

Stages (1), (2), (3), (4) and (4') are distillation stages comprising rotary evaporators having the corresponding circulatory pumps, condensers for the distillate in which the condensation heat may be used to produce vapor of a pressure of from 2 to 6 bars by cooling with water under the calculated appropriate pressure, and a connection to a suitable vacuum system. A column is connected between the evaporator and condenser at stages (2), (3), (4) and (4'). The condensers of the units of stages (4) and (4') allow rapid cooling of the distillate to temperatures of from 45° C. to 50° C.

The following discharge qualities were obtained with this arrangement.

TABLE 3

Distillation with condensation discharge temperatures in stages (1), (2) and (3) of 145° C. (about 35° C. below the temperature of the incoming vapor) and with a two-stage final distillation.

| Distillate discharge from column (FIG. 3) | Product kg/h | Reflux kg/h | Hydrolyzable chlorine ppm | Total chlorine ppm |
|---|---|---|---|---|
| 1 | 1,850 | — | 390 | 760 |
|   | 1,040 | — | 220 | 480 |
| 2 | 1,545 | 1,150 | 230 | 390 |
|   | 1,000 | 1,200 | 150 | 240 |
| 3 | 215 | 4,000 | 6 | 21 |
|   | 135 | 3,900 | 8 | 37 |
| 4 | 995 | 1,200 | 4 | 10 |
|   | 600 | 1,350 | 5 | 15 |
| 4' | 300 | 800 | 5 | 20 |
|   | 230 | 970 | 5 | 17 |

What is claimed is:

1. A process for the production of 4,4'-diisocyanatodiphenylmethane by the distillative separation of diisocyanatodiphenylmethane isomers from a polyisocyanate mixture of the diphenylmethane series obtained by phosgenating aniline/formaldehyde condensates, comprising separating said isomer from said mixture in a first distillation stage, further distilling the distillate resulting from said first stage in a second distillation stage, drawing off from 0.5 to 20%, by weight, of the quantity of product introduced into said second stage from the sump of said second stage, then subsequently separating 2,2'- and 2,4'-diisocyanatodiphenylmethane from the distillate obtained as the head product of said second stage in a third distillation stage, and finally working-up the sump product remaining from said third stage in order to obtain very pure 4,4'-diisocyanatodiphenylmethane, characterized in that (a) the temperatures of the condenser outlets of the first, second and third distillation stages are adjusted to from 130° C. to 230° C., such that the temperatures are from 10° to 50° C. below the incoming vapor temperature which is predetermined in each case by the vacuum in the distillation column, and (b) the sump remaining from said third stage is worked up in two distillation stages, such that in a first final stage, from 50 to 90%, by weight, of the sump remaining from said third stage is isolated as the head product in the form of pure 4,4'-diisocyanatodiphenylmethane, and in a second final stage, the sump of the first final stage is split into a further quantity of pure 4,4'-diisocyanatodiphenylmethane as the head product and into a distillation residue as the sump.

2. A process according to claim 1, characterized in that the reflux ratio in the first final stage is from 0.2:1 to 2:1.

3. A process according to claim 1, characterized in that the reflux ratio in the last final stage is from 0.2:1 to 3:1.

4. A process according to claim 1, characterized in that the distillates of the first final stage and the second final stage are rapidly cooled to below 50° C.

5. A process according to claim 1, characterized in that the condensation heat of the resulting distillates and refluxes is used for recovering vapor of a pressure stage of from 2 to 16 bars.

* * * * *